United States Patent
Hakamatsuka et al.

(10) Patent No.: US 6,350,462 B1
(45) Date of Patent: *Feb. 26, 2002

(54) HOLLOW POROUS CERAMIC CARRIER FOR EMBEDDING IN PATIENT FOR SUSTAINED MEDICAMENT RELEASE AND METHOD OF PREPARATION THEREOF

(75) Inventors: Yasuharu Hakamatsuka; Hiroyuki Irie; Gen Horie, all of Tokyo (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/044,549

(22) Filed: Apr. 7, 1993

Related U.S. Application Data (63) Continuation-in-part of application No. 07/810,676, filed on Dec. 19, 1991, now abandoned.

(30) Foreign Application Priority Data

Dec. 26, 1990 (JP) ............................................. 2-406852

(51) Int. Cl.$^7$ ................................................. A61K 9/52
(52) U.S. Cl. ........................ 424/422; 424/423; 424/451; 424/489; 424/464
(58) Field of Search ................................. 424/451, 473, 424/467, 484, 422, 423, 489, 464; 264/4

(56) References Cited

U.S. PATENT DOCUMENTS

| | | | |
|---|---|---|---|
| 4,293,540 A | * | 10/1981 | Shikita et al. |
| 4,479,911 A | * | 10/1984 | Fong |
| 4,542,025 A | * | 9/1985 | Tice et al. |
| 4,818,542 A | * | 4/1989 | DeLuca et al. |
| 5,051,261 A | * | 9/1991 | Mc Ginity |
| 5,051,263 A | * | 9/1991 | Barry |
| 5,068,112 A | * | 11/1991 | Samejima |
| 5,318,779 A | * | 6/1994 | Hakamatsu et al. |

FOREIGN PATENT DOCUMENTS

| | | | |
|---|---|---|---|
| EP | 0169618 | * | 1/1986 |
| JP | 55-122710 | | 9/1980 |
| JP | 59-101145 | | 6/1984 |

(List continued on next page.)

*Primary Examiner*—Raj Bawa
(74) *Attorney, Agent, or Firm*—Frishauf, Holz, Goodman, Langer & Chick, P.C.

(57) ABSTRACT

An improved porous ceramic body to be embedded in a patient for sustained release of a medicament, and a method of making the ceramic body is provided. To control the release of the medicament, the pores of the ceramic body decrease in diameter from the inner surface to the outer surface of the body whereby the pore diameter is substantially proportional to the distance from the outer surface of the carrier.

First, raw ceramic slurry is made from the blend of β-TCP, deflocculating agent, and water. Next, using a syringe the ceramic slurry is supplied to the internal region of a solvent-absorbable mold from an aperture along the inner wall surface. Then, the ceramic slurry is quickly dehydrated before thinly adhering itself onto the inner wall surface of the mold. Therefore, a preformed body having a hollow is obtained. Next, after fully being dried, the dried preformed body is fired at 1,050° C. for an hour before eventually yielding a spherical carrier for use in sustained release preparation. Substantially, the carrier is composed of a porous ceramic body which having the hollow for retaining the medicament and permits permeation of the medicament. The pore diameter corresponding to the peak value of the distribution thereof decreases toward to the outer periphery of the preformed body and yet, width of the distribution of the pore diameter becomes narrower.

7 Claims, 4 Drawing Sheets

FOREIGN PATENT DOCUMENTS

| | | |
|---|---|---|
| JP | 60-106459 | 6/1985 |
| JP | 61-47401 | 3/1986 |
| JP | 62-6522 | 2/1987 |
| JP | 64-40418 | 2/1989 |
| JP | 1-126977 | 5/1989 |
| JP | 1-197429 | 8/1989 |
| JP | 2-153886 | 6/1990 |

* cited by examiner

(1) POINT C

FIG. 9A (2) POINT D

HOLLOW POROUS CERAMIC CARRIER FOR EMBEDDING IN PATIENT FOR SUSTAINED MEDICAMENT RELEASE AND METHOD OF PREPARATION THEREOF

This application is a Continuation-In-Part, of application Ser. No. 07/810,676, filed Dec. 19, 1991 (abandoned).

BACKGROUND OF THE INVENTION

1. Field of the Invention

The present invention relates to a carrier for use in sustained release preparation for providing a medicament, in particular, anticancer agent or antibiotic, available for medical treatment such as against cancer, neoplasm and osteomyelitis to an affected part of a patient's body. The invention also relates to a method for manufacturing the carrier.

2. Description of the Related Art

Conventionally, those medicaments such as anticancer agent and antibiotic are available for medical treatment against cancer, neoplasm, or osteomyelitis. However, these medicaments more or less have grave side effects. Furthermore when dosing a patient's body with any of these medicaments, in fact, only a small portion of the dosed medicament reaches the affected part. To properly compensate for this, a novel method has been sought for selectively providing an optimum amount of the medicament to the affected part.

One method for delivering the medicament is a carrier for sustained release preparation capable of gradually releasing the medicament after burying it in the affected part of the patient's body. For example, the Unexamined Published Japanese Patent Application No. 59-101145 discloses such a method which buries a porous ceramics carrier impregnated with medicament to provide an optimum amount of the prescribed medicament to the affected part. Another Unexamined Published Japanese Patent Application No. 61-47401 discloses a carrier for use in sustained release preparation consisting of calcium-phosphate ceramic carrier having a large specific surface area and containing absorbed medicament.

Another Unexamined Published Japanese Patent Application No. 62-6522 discloses a carrier for use in sustained release preparation consisting of porous alumina granules having spatial area internally filled with a medicament. In this case, the filled medicament gradually diffuses via pores of those porous alumina granules.

Another Unexamined Published Japanese Patent Application No. 1-197429 discloses such a carrier for use in sustained release preparation which, except for an aperture to permit impregnation of a medicament, covers the surface of porous ceramic body permitting impregnation of the medicament in pores each having 10 to 30 $\mu$m of diameter by means of film having pores respectively having 10 $\mu$m and less than of diameter and 300 $\mu$m and less than of thickness.

These preceding Unexamined Published Japanese Patent Application No. 59-101145 and No. 61-47401 respectively disclose the art which initially requires a porous ceramic carrier to absorb the medicament, and then buries the porous ceramic carrier in the affected part of the patient body thereby permitting the medicament to be released from the porous ceramic carrier. Nevertheless, most of the medicament therein are not chemically absorbed in the porous ceramic carrier, but instead, medical ingredients are physically absorbed in this carrier. In consequence, immediately after being buried in the patient's body, the medicament is quickly released from the porous ceramic carrier to result in the failure to constantly provide the medical ingredients to the affected part for an extended time. Even when varying the ratio and diameter of pores of the porous ceramic carrier, actually, it is quite difficult for this carrier to properly control the amount of the released medicament.

On the other hand, the carrier for use in sustained release preparation proposed by the Examined Published Japanese Patent Application No. 62-6522 is manufactured by blending deceptive pore forming material with alumina powder followed by a shaping process and a firing process. Distribution of pore diameter of porous carrier produced by executing those processes mentioned above is dependent on the dispersed condition of the pore forming material. Therefore, if the available pore forming material unevenly disperses, then, continuous pores are generated in a region where the pore forming material of the porous carrier is concentrated. In this case, a local average of pore diameter noticeably exceeds a total average of pore diameter of the porous carrier. Therefore, the pore diameter in this region affects the sustained release characteristic of the medicament by causing the carrier to fully release the medicament in a very short period of time.

As is clear from the above description, the carrier for use in sustained release preparation disclosed in the Examined Published Japanese Patent Application No. 62-6522 tend to vary the sustained release characteristic of the medicament among carriers according to the dispersed condition of the pore forming material. As a result, any of these conventional carriers quickly release the medicament to incur unwanted side effect to the patient's body. On the other hand, any of these conventional carriers release a little amount of the medicament to nullify the effect of medical treatment.

On the other hand, the other carrier for sustained release preparation disclosed in the Unexamined Published Japanese Patent Application No. 1-197429 described above is buried in the affected part of the patient's body without shutting off the aperture provided on the surface of the porous ceramic carrier. This in turn causes the medicament to leak out of the aperture by such an amount in excess of the prescribed dosage.

As described above, any of those conventional carriers for use in sustained release preparation cannot properly and fully exert the function of the carrier itself to stably provide the medicament to the affected part of the patient's body for a long period of time.

SUMMARY OF THE INVENTION

The primary object of the invention is to provide a novel carrier for use in sustained release preparation, which is capable of selectively providing an optimum amount of a medicament to the affected part for a long period of time after being buried in the patient's body.

Another object of the invention is to provide a novel carrier for use in sustained release preparation, which is capable of stably maintaining the sustained release characteristic of a medicament without varying it at all.

Another object of the invention is to provide a novel method for manufacturing a carrier for sustained release preparation to permit manufacturers to easily produce the carrier.

Specifically, the invention provides a novel carrier for use in sustained release preparation, which comprises a porous ceramic body having a cavity for retaining a medicament and which controls release of the medicament. The porous ceramic body is capsule-shaped and has pores extending inwardly of the outer periphery thereof, each of which has a diameter substantially proportional to the distance from a outer periphery of the porous ceramic body.

Furthermore the present invention provides a novel carrier for use in sustained release preparation, which comprises a porous ceramic body having a hollow for retaining a medicament and which controls release of the medicament, wherein the porous ceramic body is capsule-shaped and has pores, and has a pore rate which decrease toward to the outer periphery of the porous ceramic body.

Furthermore, the present invention provides a novel method for manufacturing a carrier for use in sustained release preparation, which carrier comprises a porous ceramic body having a hollow for retaining a medicament and controls release of the medicament. The method comprises a step of preparing a raw material ceramics slurry, a step of preparing a preformed body containing a hollow by causing the raw material ceramic slurry to adhere on an inner wall surface of a solvent-absorbable mold, a step of firing the preformed body, thereby obtaining the porous ceramic body is capsule-shaped and has pores, each of which has a diameter substantially proportional to the distance from a outer periphery of the porous ceramic body.

Furthermore, the present invention provides a novel method for manufacturing a carrier for use in sustained release preparation, which carrier comprises a porous ceramic body having a hollow cavity for retaining a medicament and controls release of the medicament. The method comprises a step of preparing a slurry of the raw material for forming the porous ceramic body, a step of preparing a preformed hollow body containing a cavity by coating the raw material ceramic slurry on an inner wall surface of a solvent-absorbable mold, a step of firing the preformed body, thereby obtained the porous ceramic body is capsule-shaped and has pores, and has a pore rate which decreases toward to the outer periphery of the porous ceramic body.

Next, details of the carrier for use in sustained release preparation and the related manufacturing methods are described below.

The carrier for use in sustained release preparation of the present invention has a cavity for retaining a medicament inside of a porous ceramic body which is capable of constantly releasing an optimum amount of the medicament. Therefore, the medicament can be retained in the cavity by immersing the carrier in solution of the medicament. When the carrier internally retaining the medicament is buried in a patient's body, the medicament is gradually released through pores of the porous ceramic body, thereby constantly releasing an optimum amount of the medicament for a long period of service life.

In the carrier of the present invention, it is also particularly preferred to use such a porous ceramic body having the pore diameter corresponding to the peak value of the distribution thereof to decrease toward to the outer periphery of the porous ceramic body.

Note that the distribution of pore diameter means a frequency of appearance of the pore against the particular pore diameter thereof, the porous are contained into the region of the porous ceramic body, which exist at the same distance from the external surface of the porous body and of which thickness is sufficiently thin compared to thickness of the all porous body.

Substantially, in the vicinity of the outer periphery, the porous ceramic body is devoid of large pores, but instead, all pores are dense structure. Owing to this structural advantage, the porous ceramic body is capable of retaining the medicament in the hollow thereof for a long period of service life, and yet, the porous ceramic body can maintain the released amount of the medicament constant.

In the present invention, the released amount of the medicament can properly be controlled through varying the medicament-permeability and diffusion characteristic of the porous ceramic body by means of varying the pore ratio, the pore diameter, and thickness of the porous ceramic body.

Material for composing the porous ceramic body of the present invention may be selected from calcium phosphate containing distinct bioaffinity, alumina, zirconia or mixture of these. In particular, the calcium phosphate ceramics is ideally suited for preparing the carrier for use in sustained release preparation of the present invention particularly in the case of burying it in the bone tissue of a patient for medically treating osteometitis.

As is apparent from the above description, according to the carrier for use in sustained release preparation of the present invention, when the carrier retaining the medicament is buried in the affected part of the patient's body, the medicament is gradually released via pores of the porous ceramic body, and thus, an optimum amount of the medicament can directly and selectively be provided to the affected part. As a result, the effect of medical treatment can be fully achieved merely by internally providing a slight amount of the medicament, and yet, effectively minimize grave side effects.

On the other hand, according to the method of manufacturing the carrier for use in sustained release preparation of the present invention, a slurry of the raw material for the ceramic is deposited on the inner wall surface of a solvent-absorbable mold to cause water in slurry to be absorbed in the mold very quickly, thus producing a preformed body having a hollow center.

Also, according to the method of manufacturing the carrier for use in sustained release preparation of the present invention, a plurality of parts may individually be formed at the initial step before preparing a preformed body by combining these parts with each other. For example, when making up a preformed body, initially, semispherical parts are molded, and then these parts are bonded together to complete a preformed body.

As is clear from the above description, according to the method of manufacturing the carrier for use in sustained release preparation of the present invention, the carrier can easily be manufactured.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Referring now to the accompanying drawings, detail of the carrier for use in sustained release preparation according to an embodiment of the invention is described below.

Figure 1:
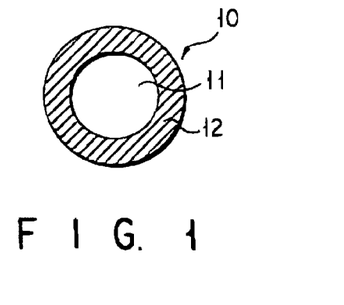
FIG. 1 is a sectional view of the carrier for use in sustained release preparation according to an embodiment of the present invention.

The reference numeral 10 shown in FIG. 1 designates a carrier for use in sustained release preparation composed of a spherical porous ceramic body 12 having a hollow 11. The hollow 11 is retaining a solution of a medicament (medicament solution). Concretely, the porous ceramic body 12 can be made from calcium phosphate like β-tricalcium phosphate (β-TCP) or hydroxylapatite (HAP), or alumina, or zirconium, or mixture of these. In particular, it is desired that the porous ceramic body 12 be made from calcium phosphate containing distinct bioaffinity.

Substantially, the porous ceramic body 12 has about 8 mm of diameter. The porous ceramic body 12 has such a pore rate permitting the medicament solution retained in the hollow 11 to permeate it. More preferably the porous ceramic body 12 has about 30% of pore rate.

A most preferred porous ceramic body 12 has the pore diameter corresponding to the peak value of the distribution thereof to decrease region toward outer periphery of the porous ceramic body 12, and yet, the closer the outer periphery the narrower the width of the distribution of the pore diameter. In other words, the mean of the diameter of pores of the porous ceramic body 12 decreases along the radial direction, and yet toward to the outward direction. For example, in the inner region of the porous ceramic body 12 faced on the hollow 11, the peak value of the distribution of the pore was about 5 µm and the pore rate was about 30%, while in the outer region near the outer periphery, the peak value of the distribution was about 1 µm and less than and the pore rate was about 30%.

FIGS. 7–9A and 9B illustrate the pore rate or pore distribution in the ceramic carrier of the invention.

Figure 7:
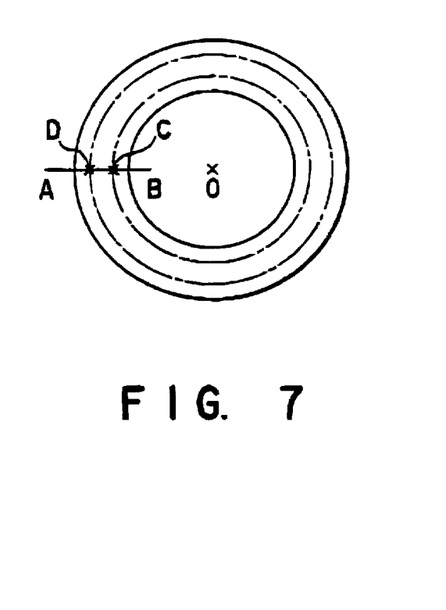
FIG. 7 is a sectional view of an embodiment of the inventive carrier.
Figure 8:
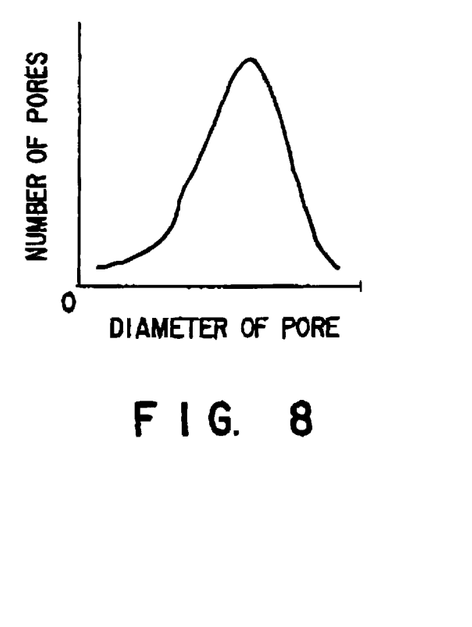
FIG. 8 is a curve showing the distribution of pore diameters in the wall of the carrier.

Referring to FIG. 7, a cross-sectional view of the inventive carrier is shown. In FIG. 7, point O is the center of the carrier, A–B is a line connecting the internal surface and external surface of the shell, C or D is a selected one of the sequent points on line A–B. For the purposes of this explanation, it is assumed that a sphere defined by points equidistance from the same center O as the carrier has on its circumference, a point C or D (hereinafter referred to as "circumference C or D").

The term "distribution of pore diameter" means the distribution of pores which have a specific diameter and are formed in the circumference of the assumed sphere. For the purposes of explanation of the meaning of "distribution of pore diameter" a hypothetical distribution is shown by the curve in FIG. 8, where diameters are plotted on abscissas, and the number of pores having the specific pore diameter (plotted in the abscissas) is plotted on ordinate.

In the case of the carrier shown in FIG. 7, there is a "pore diameter" which is the diameter corresponding to a peak value in the distribution of pore diameters, that is the pore diameter that the largest number of pores have in common. The diameter of pores formed in circumference D differs from that of pores formed in circumference C. That is to say, the pore diameter corresponding to the peak value in the distribution of pore diameter relating to circumference D is smaller than that in the distribution of pore diameter relating to circumference C.

Figure 9A:
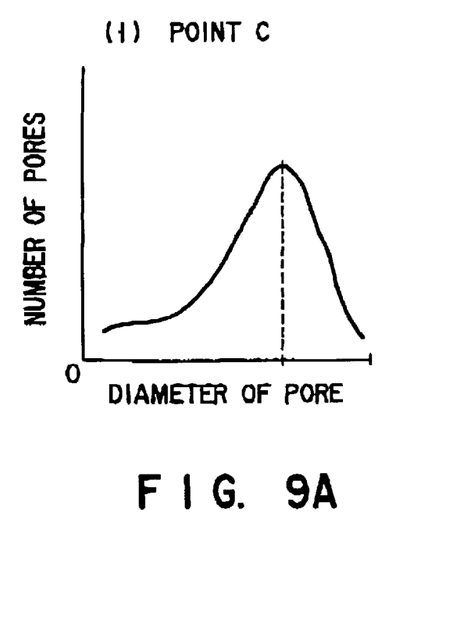
FIGS. 9A and 9B are curves showing the distribution of pore diameters at points C and D of FIG. 7.
Figure 9B:
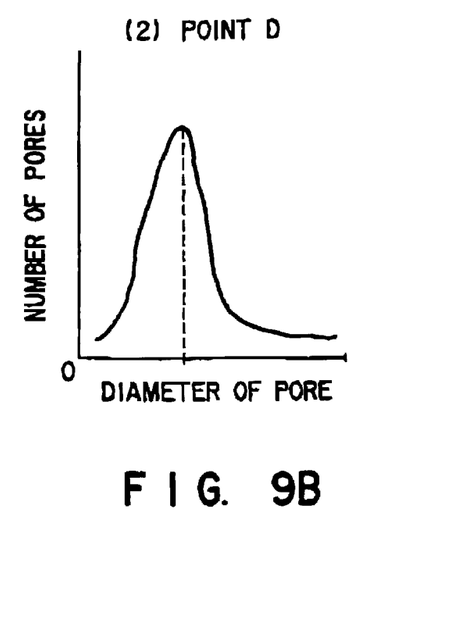

Furthermore, the inventive carrier has a pore distribution such that the closer the pores are to the external surface of the carrier, the narrower the range of the distribution of the pore diameter. In other words, as shown in FIGS. 9A and 9B, the range of the diameter distribution of pores formed in the circumference D (closer to outer shell of the carrier) is narrower than that of pores formed in circumference C.

To embody the invention, actually, the carrier 10 for use in sustained release preparation was manufactured by sequentially executing those processes described below.

First, 30 grams of β-TCP powder is synthesized by applying conventional mechano-chemical reaction. Next 15 ml of deflocculating agent and 25 ml of water are added to the synthesized β-TCP powder, and then the obtained composition is properly blended and stirred to prepared raw-material ceramic slurry 22. Note that not only water is available for blending the above composition, but any conventional solvent may also be made available.

Figure 2:
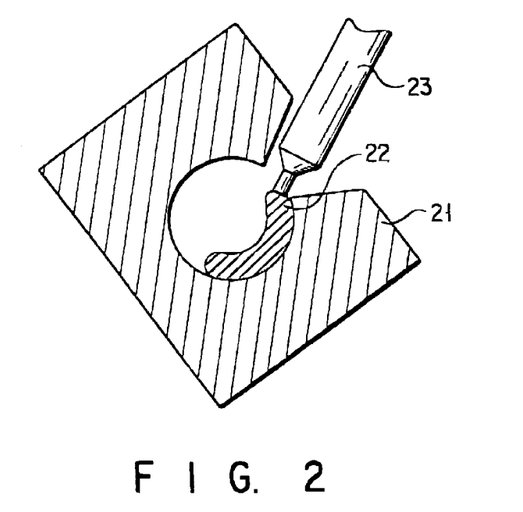
FIG. 2 is a partial sectional view showing adhesion of raw-material ceramic slurry to the inner wall surface of a mold while executing the method of manufacturing the carrier for use in sustained release preparation of a embodiment of the present invention.

Next, the prepared ceramic slurry 22 is filled in a syringe 23. Then, as shown in FIG. 2, using the syringe 23, the fluid ceramic slurry 22 is supplied into a mold 21 from an aperture along the inner wall surface, said mold 21 is made from solvent-absorbable material, such as plaster of pairs, and has a spherical cavity of which an inner diameter is about 8 mm. As a result, only water is quickly absorbed in the mold 21 from the fluid ceramic slurry 22 in contact with the inner wall surface of the mold 21. In consequence, the ceramic slurry 22 gains substantial viscosity, thereby thinly adhering itself to the inner wall surface of the mold 21.

Figure 3:
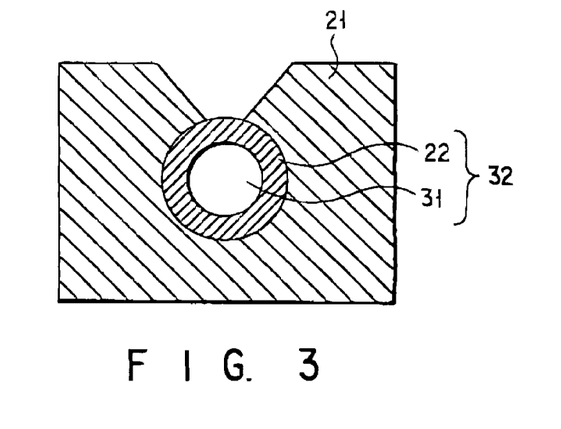
FIG. 3 is a sectional view of a preformed body produced by executing the method of manufacturing the carrier for use in sustained release preparation according to an embodiment of the present invention.

According to the procedure as described above, the mold 21 internally containing viscose ceramic slurry 22 is continuously rotated. This causes the viscose ceramic slurry 22 to evenly adhere to the whole inner surface of the mold 21, and finally, as shown in FIG. 3, a preformed body 32 having a hollow 31 and capsule-shaped is obtained.

While causing the viscose ceramic slurry 22 to adhere to the inner wall surface of the mold 21 on the way of producing the preformed body 32, particles of β-TCP in the ceramic slurry 22 move in conjunction with water being absorbed in the inner wall surface of the mold 21, and then moved particles uniformly deposit themselves in the region close to the surfaces of the ceramic slurry 22 and the mold 21 in contact with each other. In particular, the finer the particle size, the higher the rate of occurrence of this advantageous effect. Owing to this effect, pores existing in the vicinity of the surfaces of the ceramic slurry 22 and the mold 21 in contact with each other, in other words, those pores existing in the superficial region of the preformed body 32 are filled with particles of β-TCP. In consequence, the pore diameter corresponding to the peak value of the distribution thereof decreases toward to the outer periphery of the preformed body 32, and yet, width of the distribution of the pore diameter becomes narrower.

Next, the preformed body 32 is fully dried and then fired at 1,050° C. for an hour, thereby obtaining a carrier 10 for use in sustained release preparation.

The sustained release characteristic of the medicament retained in the carrier 10 can properly be controlled by varying the mean diameter of pores on the most outer superficial regions of the porous ceramic body 12, where the mean diameter of these pores is one of important factors to determine the sustained release characteristic of the medicament in the carrier 10. Concretely, the mean diameter of those pores of the porous ceramic body 12 is variable by, for example, varying the mean diameter of β-TCP particles, varying the blend ratio between particles of β-TCP and water or by varying temperature for firing the preformed body 32.

Figure 4:
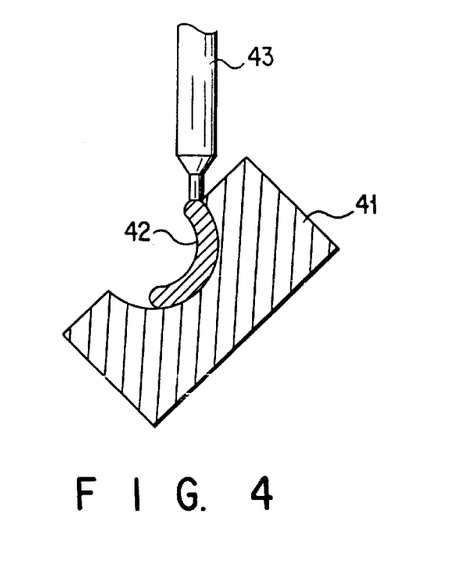
FIG. 4 is a partial sectional view designating adhesion of raw-material ceramic slurry to the inner wall surface of a mold while executing the method of manufacturing the carrier for use in sustained release preparation according to another embodiment of the present invention.
Figure 5:
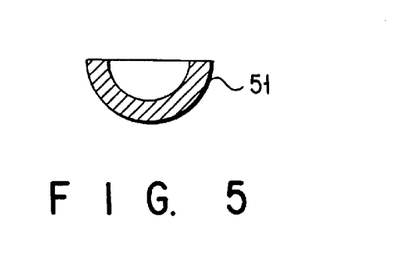
FIG. 5 is a sectional view of a semispherical part produced by executing the method of manufacturing the carrier for use in sustained release preparation according to another embodiment of the present invention.

The invention also provides another method of manufacturing the carrier 60 for use in sustained release preparation shown in FIG. 4. For example, initially, using a syringe 43, fluid ceramic slurry 42 is supplied into a mold 41 having a semispherical cavity of which of inner diameter is about 8 mm along the inner surface so that the fluid slurry 42 adheres to and coats inner wall surface of the mold 41. After being dried, the viscose ceramic slurry 42 is released from the mold 41, and then, as shown in FIG. 5, a semispherical preformed body 51 is obtained. These sequential processes are again executed before eventually obtaining a pair of semispherical preformed body 51.

Figure 6:
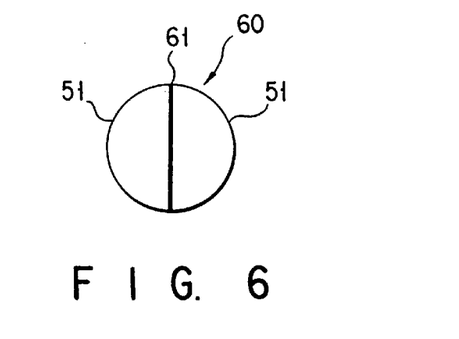
FIG. 6 is a front view of the carrier for use in sustained release preparation produced by executing the method of manufacturing the carrier according to another embodiment of the present invention.

Next, as shown in FIG. 6, using biological cement 61 comprising of β-TCP and aqueous solution of citric acid, these semispherical preformed body 51 and 51 are bonded together. After a drying process, the spherical preformed body is fired at 1,050° C. for an hour before eventually completing the carrier 60 for use in sustained release preparation.

The invention thus provides those complete carriers 10 and 60. The completed carrier 10 for example is then immersed in solution containing medicament like antibiotic or anticancer agent. Next, the carrier internally retaining the medicament solution is stored in decompressed atmosphere. As a result, the carrier 10 can securely retain the medicament solution in the hollow 11 after permeating it via pores of the porous ceramic substance 12.

To evaluate performance characteristic of the produced carrier 10 for example, the carrier 10 internally storing the medicament solution was immersed in physiological saline, and then the density of released medicament was measured based on the passage of time.

In the method of the present invention for manufacturing a carrier for use in a sustained release preparation, it is also possible to add a surfactant to the ceramic raw material slurry to prepare a foamed slurry. Use of such a foamed slurry makes it possible to prepare easily a carrier for use in a sustained release preparation, said carrier having a relatively large average pore diameter of about 5 to 100 μm.

The present inventors conducted a comparative test to demonstrate the differences between the present invention and prior art in the sustained release characteristics of the carrier. In the comparative test, the carrier for each of the present invention and prior art was made of β-TCP. Also, these carriers were substantially equal to each other in the inner and outer diameters, average pore diameter, and porosity. Further, two additional experiments were conducted with the carriers for the present invention and the prior art made different from each other in the average pore diameter and in the porosity, respectively.

The carrier was impregnated with a medicament under a reduced pressure so that the medicament was introduced into a cavity of the carrier. To be more specific, each carrier was placed in a vessel containing sufficient dibekacin (antibiotic) solution used as the medicament, to cover the carrier. Then, the vessel containing the carrier and dibekacin solution was put in a hermetically sealed container and the container evacuated for about one hour. The vacuum was relieved and the carrier removed from the vessel was found to be impregnated with the medicament, so as to retain the medicament in the cavity. The amount of dibekacin retained in each carrier was in an amount of 3 mg. The reduced pressure maintained for preparing impregnated carrier is preferably at least about $10^{-2}$ Torr and more preferably about $10^{-5}$ Torr.

The carrier impregnated with the medicament was dipped in a physiologic saline to permit the medicament held within the carrier to be replaced by the physiological saline. Changes with time in the release amount of the medicament from within the carrier were measured as follows. Specifically, each carrier was dipped in 8 ml of physiological saline, and the resultant system was left to stand at 37° C. In the measuring step, the physiological saline was renewed entirely to obtain a test solution. The medicament concentration of the test solution was calculated by the formula given below based on a microbiological measuring method (Agar-well method) using *Bacillus subtilis* ATCC 6633 as a test bacteria:

Release rate $(\%)=A/B\times 100$ where, A is "measured strength (μg, titer)/ml×dipping solution amount (ml)" and B is "dibekacin titer [initial content] (μg, titer)".

Figure 10:
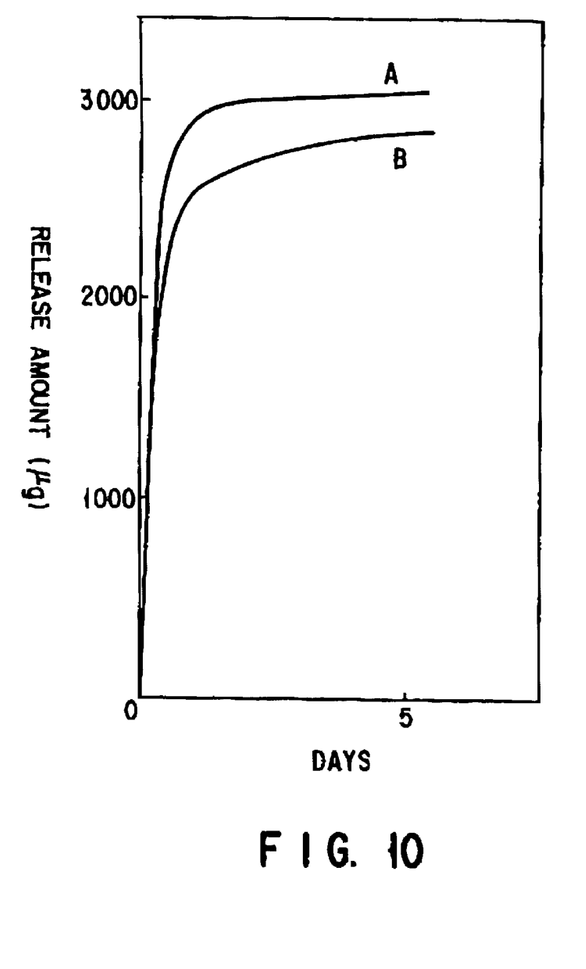
FIGS. 10 and 11 show the release rate of medicament with time, for two different carriers as compared with non-inventive carriers.
Figure 11:
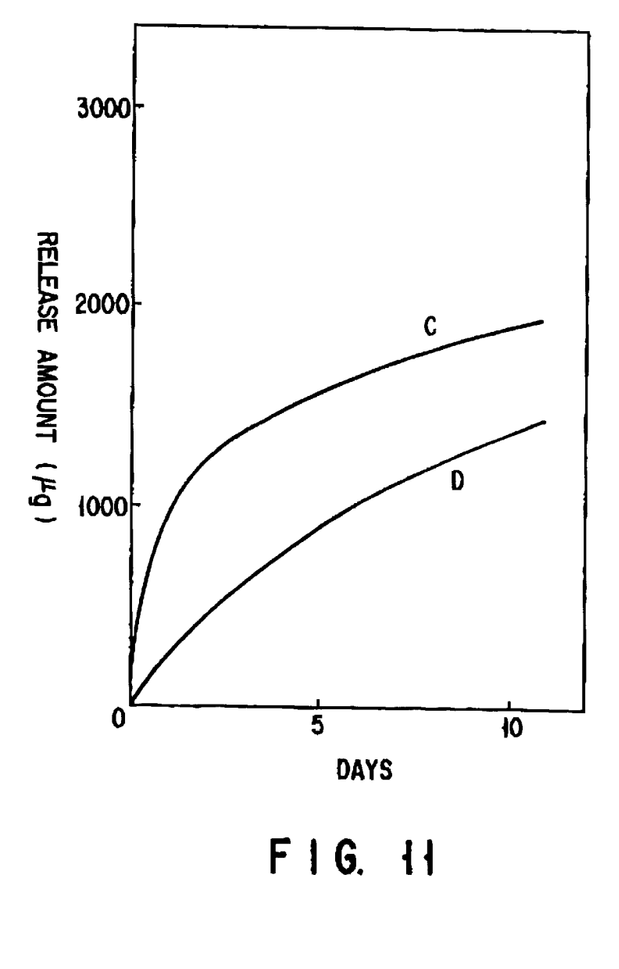

The second measurement et seq. were similarly performed. FIGS. 10 and 11 show the accumulated values of the medicament concentration thus calculated as release amount (μg).

FIG. 10 shows the case where the carrier for the sustained release preparation was 5 mm in outer diameter, 4 mm in inner diameter, had a pore size distribution of 5 to 100 μm, an average pore diameter of 25 μm, and a porosity of about 25%. Curve A in FIG. 10 shows the prior art in which the outer and inner surface regions are substantially the same in the pore size and porosity, with curve B denoting the carrier of the present invention in which the average pore size was 50 μm in the inner surface region and 10 μm in the outer surface region. In the carrier of the present invention, the average pore size was monotonously or continuously decreased from 50 μm in the inner surface region toward 10 μm in the outer surface region.

As seen from curve A, the medicament was rapidly released in the initial stage of the dipping of the carrier in the physiological saline in the prior art. In this case, substantially all the medicament was released from the carrier in about 5 days. In the carrier of the present invention, however, release of the medicament was much suppressed in the initial stage of the dipping of the carrier in the physiological saline, as seen from curve B as a matter of fact, release of the medicament was not finished 5 days later.

FIG. 11 covers the case where the carrier was 5 mm in outer diameter, 4 mm in inner diameter, had a pore size distribution of 0.5 to 2 μm, an average pore diameter of 1 μm, and a porosity of about 15%. Curve C in FIG. 11 shows the prior art in which the outer and inner surface regions are substantially the same in pore size and porosity, with curve D denoting the carrier of the present invention in which the average pore size was 2 μm in the inner surface region and 0.5 μm in the outer surface region. In the carrier of the present invention, the average pore size was monotonously or continuously decreased from 2 μm in the inner surface region toward 0.5 μm in the outer surface region.

As seen from curve C, the medicament was rapidly released in the initial stage of the dipping of the carrier in the physiological saline in the prior art. In this case, the medicament was released from the carrier in such a large amount as about 1900 μg in 10 days. In the carrier of the present invention, however, release of the medicament was much suppressed in the initial stage of the dipping of the carrier in the physiological saline, as seen from curve D. As a matter of fact, the amount of the medicament released from the carrier in the initial 10 days was only about 1300 μg, which was smaller by as much as about 600 μg than in the prior art denoted by curve C.

As apparent from the experimental data shown in FIGS. 10 and 11, the carrier used in the present invention permits maintaining a sustained release of the medicament over a longer period than in the prior art.

As is apparent from the above description, according to those novel carrier 10 and 60 for use in sustained release preparation of the present invention, after burying, for example, the carrier 10 in the patient's body close to the affected part, the medicament solution retained in the hollow 11 is released via pores of the porous ceramic body 12. By virtue of this effect, the carrier 10 can constantly released an optimum amount of the medicament for a very long period of time. As a result, since the carrier 10 can directly and selectively provide the medicament to the affected part of the patient's body, the actual effect of medical treatment can be substantially promoted even when dosing a little amount of the medicament, and yet, occurrence of grave side effects can be effectively minimized.

Also, according to the present invention, the release amount of the medicament can be controlled by modify permeability of the medicament solution of by properly varying either the pore rate, pore diameter, or thickness of the porous ceramic body.

Even when manufacturing a large number of carriers for use in the sustained release preparation the present invention, fluctuation of the sustained release characteristic of the medicament among the carriers can remain minimum. Therefore, it is able to prevent the disadvantage of that one of the carriers quickly releases the medicament to incurs grave side effect to the patient's body, the other releases a little amount of the medicament to nullify the effect of medical treatment from occurrence otherwise caused by uneven sustained release characteristic among carriers. As a result, whenever making use of the carrier for use in sustained release preparation of the present invention, all the medical specialists can securely look forward to satisfactory effect of medical treatment generated by stable effect of the medicament retained in the carrier of the present invention us.

In the present invention, also, the porous ceramic body is composed of β-TCP containing distinct bioaffinity and water-absorbable property. By virtue of these advantageous functions, there is no need of extracting the carrier from the patient's body even after the whole medical treatment. After burying the carrier for use in the sustained release preparation of the present invention in the bone organization of a patient's body, the carrier composed of β-TCP is substituted by the patient's bone after a certain period of time is past, and thus, based on this advantage, β-TCP is ideally suited for use.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. In a porous ceramic carrier for use in sustained release preparation to be embedded in the body of a patient for sustained release of a medicament, the improvement which comprises a porous ceramic body shaped in a capsule form with a shell of porous ceramic having an outer surface and an inner surface, said inner surface defining a cavity for retaining a medicament, said porous ceramic body having pores communicating with one another to define a medicament release path from said inner surface to said outer surface to communicate said cavity with said outer surface and permit release of medicament from said cavity, said pores decreasing in diameter from the inner surface to the outer surface of said porous ceramic body whereby the pore diameter is substantially proportional to the distance from the outer surface of the carrier; and wherein the material forming the porous ceramic body is selected from the group consisting of calcium phosphate, alumina, zirconia and mixtures thereof.

2. A carrier according to claim 1, wherein the porous ceramic body is composed of calcium phosphate.

3. A method for manufacturing a carrier for use in sustained release preparation, which carrier comprises a porous ceramic body formed in a capsule shape and having a hollow cavity for retaining a medicament and controls release of the medicament, said method comprising sequentially performing the following steps:

preparing a slurry of raw material for forming the ceramic body;

introducing the slurry into a solvent absorbable mold;

preparing a preformed hollow body containing a cavity defining a shell by spreading the slurry to form an evenly adhering coating on the inner surface of the solvent-absorbable mold; and calcining the preformed body, thereby obtaining said porous ceramic body which is capsule-shaped and has pores each having a diameter substantially proportional to the distance from an outer periphery of said porous ceramic body; and wherein the material forming the porous ceramic body is selected from the group consisting of calcium phosphate, alumina, zirconia and mixtures thereof.

4. The method of claim 3, wherein the porous ceramic body is composed of calcium phosphate.

5. The method of claim 3, wherein said shell is formed in several parts, further comprising, before the calcining step, the step of assembling the shell to define an enclosed cavity.

6. The method of claim 3, wherein the step of preparing a raw material slurry comprises adding a deflocculating agent and water to a porous ceramic raw material powder prepared by a mechanochemical method, and stirring the resultant mixture.

7. The method of claim 6, wherein the step of preparing a raw material slurry further comprises adding a surfactant.

* * * * *